US009084596B2

(12) United States Patent
Stanley et al.

(10) Patent No.: US 9,084,596 B2
(45) Date of Patent: Jul. 21, 2015

(54) SUTURE CLAMP AND GASTROINTESTINAL SUTURE ANCHOR SET DEVICE USING SAME

(75) Inventors: Cleon P. Stanley, Bloomington, IN (US); Jeffry S. Melsheimer, Springville, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 604 days.

(21) Appl. No.: 13/405,852

(22) Filed: Feb. 27, 2012

(65) Prior Publication Data
US 2013/0226237 A1 Aug. 29, 2013

(51) Int. Cl.
A61B 17/04 (2006.01)
A61B 17/00 (2006.01)
A61B 17/06 (2006.01)

(52) U.S. Cl.
CPC ......... *A61B 17/0401* (2013.01); *A61B 17/0469* (2013.01); *A61B 17/0487* (2013.01); *A61B 2017/00818* (2013.01); *A61B 2017/0417* (2013.01); *A61B 2017/0479* (2013.01); *A61B 2017/06052* (2013.01)

(58) Field of Classification Search
CPC ........... A61B 17/0401; A61B 17/0487; A61B 2017/0409; A61B 2017/0414; A61B 2017/0438; A61B 2017/0446; A61B 2017/0454; A61B 2017/0456; A61B 2017/0458; A61B 2017/0459; A61B 2017/0488; A61B 2017/06052
USPC ......... 606/120, 135, 136, 139, 142, 144, 147, 606/148, 151, 157, 158, 224–232
See application file for complete search history.

(56) References Cited

U.S. PATENT DOCUMENTS

| 600,887 | A | * | 3/1898 | Pettit | 606/120 |
|---|---|---|---|---|---|
| 3,976,079 | A | * | 8/1976 | Samuels et al. | 606/232 |
| 4,291,698 | A | * | 9/1981 | Fuchs et al. | 606/232 |
| 4,378,802 | A | * | 4/1983 | Ersek | 606/157 |
| 4,418,694 | A | * | 12/1983 | Beroff et al. | 606/158 |
| 4,424,810 | A | * | 1/1984 | Jewusiak | 606/142 |
| 4,705,040 | A | * | 11/1987 | Mueller et al. | 606/108 |
| 4,750,492 | A | * | 6/1988 | Jacobs | 606/230 |
| 4,976,722 | A | * | 12/1990 | Failla | 606/157 |
| 5,074,846 | A | * | 12/1991 | Clegg et al. | 604/164.1 |
| 5,078,731 | A | * | 1/1992 | Hayhurst | 606/232 |
| 5,112,310 | A | * | 5/1992 | Grobe | 604/175 |
| 5,121,836 | A | * | 6/1992 | Brown et al. | 206/63.3 |
| 5,129,511 | A | * | 7/1992 | Brown et al. | 206/63.3 |
| 5,154,283 | A | * | 10/1992 | Brown | 206/63.3 |

(Continued)

FOREIGN PATENT DOCUMENTS

WO 2009027860 3/2009

*Primary Examiner* — Ryan Severson
(74) *Attorney, Agent, or Firm* — Liell & McNeil

(57) ABSTRACT

A gastrointestinal suture anchor set device includes a pusher slidably received in a needle. A suture clamp assembly includes an anchor attached to one end of a length of the suture, which is slidably received in a sequence of passages defined by a suture clamp in a high profile sliding configuration. The anchor is received in the distal end of the needle with the suture extending outside of the needle. The clamp includes a series of disks movable to a low profile clamped configuration at which different segments of the suture are clamped between faces of adjacent disks. The series of disks define a sequence of suture passages that are segments of a tortuous pathway through the clamp traversed by the suture.

20 Claims, 3 Drawing Sheets

(56) References Cited

U.S. PATENT DOCUMENTS

| | | | | |
|---|---|---|---|---|
| 5,160,339 A | * | 11/1992 | Chen et al. | 606/158 |
| 5,167,627 A | * | 12/1992 | Clegg et al. | 604/103.03 |
| 5,171,251 A | * | 12/1992 | Bregen et al. | 606/151 |
| 5,258,015 A | * | 11/1993 | Li et al. | 606/232 |
| 5,269,809 A | * | 12/1993 | Hayhurst et al. | 606/232 |
| 5,282,832 A | * | 2/1994 | Toso et al. | 606/232 |
| 5,307,924 A | * | 5/1994 | Manosalva et al. | 206/63.3 |
| 5,318,543 A | * | 6/1994 | Ross et al. | 604/170.01 |
| 5,330,442 A | * | 7/1994 | Green et al. | 606/232 |
| 5,409,499 A | * | 4/1995 | Yi | 606/151 |
| 5,462,558 A | * | 10/1995 | Kolesa et al. | 606/139 |
| 5,474,572 A | * | 12/1995 | Hayhurst | 606/232 |
| 5,531,699 A | * | 7/1996 | Tomba et al. | 604/170.02 |
| 5,626,614 A | * | 5/1997 | Hart | 606/232 |
| 5,645,553 A | * | 7/1997 | Kolesa et al. | 606/157 |
| 5,665,109 A | * | 9/1997 | Yoon | 606/232 |
| 5,695,505 A | * | 12/1997 | Yoon | 606/157 |
| 5,810,853 A | * | 9/1998 | Yoon | 606/151 |
| 5,951,590 A | | 9/1999 | Goldfarb | |
| 5,984,933 A | | 11/1999 | Yoon | |
| 6,010,525 A | * | 1/2000 | Bonutti et al. | 606/232 |
| 6,159,234 A | * | 12/2000 | Bonutti et al. | 606/232 |
| 6,273,903 B1 | * | 8/2001 | Wilk | 606/219 |
| 6,319,271 B1 | * | 11/2001 | Schwartz et al. | 606/232 |
| 6,582,443 B2 | * | 6/2003 | Cabak et al. | 606/151 |
| 6,974,462 B2 | * | 12/2005 | Sater | 606/232 |
| 7,435,251 B2 | * | 10/2008 | Green | 606/232 |
| 7,686,830 B2 | * | 3/2010 | Collier et al. | 606/232 |
| 7,867,253 B2 | * | 1/2011 | McMichael et al. | 606/232 |
| 8,382,772 B2 | * | 2/2013 | Rotella et al. | 606/130 |
| 8,753,373 B2 | * | 6/2014 | Chau et al. | 606/232 |
| 2001/0021862 A1 | * | 9/2001 | Bonutti et al. | 606/232 |
| 2002/0077662 A1 | * | 6/2002 | Bonutti et al. | 606/232 |
| 2003/0009196 A1 | * | 1/2003 | Peterson | 606/232 |
| 2003/0171759 A1 | * | 9/2003 | Sadler et al. | 606/135 |
| 2003/0229361 A1 | * | 12/2003 | Jackson | 606/144 |
| 2004/0059359 A1 | * | 3/2004 | Wilson, Jr. | 606/157 |
| 2004/0102809 A1 | * | 5/2004 | Anderson | 606/232 |
| 2004/0199178 A1 | * | 10/2004 | Small | 606/120 |
| 2005/0004602 A1 | * | 1/2005 | Hart et al. | 606/232 |
| 2005/0149120 A1 | * | 7/2005 | Collier et al. | 606/232 |
| 2005/0165421 A1 | * | 7/2005 | Wilson et al. | 606/151 |
| 2005/0165422 A1 | * | 7/2005 | Wilson | 606/151 |
| 2005/0165423 A1 | * | 7/2005 | Gallagher et al. | 606/151 |
| 2005/0165424 A1 | * | 7/2005 | Gallagher et al. | 606/151 |
| 2006/0184200 A1 | * | 8/2006 | Jervis | 606/232 |
| 2007/0049970 A1 | | 3/2007 | Belef et al. | |
| 2007/0073345 A1 | * | 3/2007 | Pipenhagen et al. | 606/232 |
| 2007/0093858 A1 | | 4/2007 | Gambale et al. | |
| 2007/0276417 A1 | * | 11/2007 | Mendes, Jr. et al. | 606/157 |
| 2008/0140117 A1 | | 6/2008 | Bonutti et al. | |
| 2009/0012537 A1 | * | 1/2009 | Green | 606/139 |
| 2009/0062853 A1 | * | 3/2009 | McMichael et al. | 606/232 |
| 2009/0240266 A1 | * | 9/2009 | Dennis | 606/151 |
| 2012/0059414 A1 | * | 3/2012 | Roorda | 606/232 |
| 2012/0065648 A1 | * | 3/2012 | Roorda | 606/148 |
| 2013/0079820 A1 | * | 3/2013 | Stanley | 606/232 |
| 2013/0218205 A1 | * | 8/2013 | Stanley | 606/232 |

\* cited by examiner

US 9,084,596 B2

SUTURE CLAMP AND GASTROINTESTINAL SUTURE ANCHOR SET DEVICE USING SAME

TECHNICAL FIELD

The present disclosure relates generally to suture clamps used in surgical procedures, and more particularly to a suture clamp that is a portion of a gastrointestinal suture anchor set device.

BACKGROUND

In order to assist in the long term placement of gastric catheters and feeding tubes, a patient's stomach must often be lifted against the abdominal wall. Generally, the stomach should be lifted against the abdominal wall for a duration long enough for a tract to form between the outside of the patient's body and the stomach. In one strategy, three gastric suture anchors may be inserted into the patient's stomach in a triangular pattern surrounding the intended central location for a forthcoming gastric catheter or feeding tube. After each gastric suture anchor is lifted toward the abdominal wall, an external suture clamp is utilized to clamp onto the surface of the suture adjacent the patient's skin. Tension in the suture between the clamp and the anchor maintain the patient's stomach lifted against the abdominal wall. Thereafter, a gastric catheter or feeding tube is inserted through the skin into the stomach, through the central portion surrounded by the triangular pattern of anchor clamp combinations. After the tract from the patient's skin to the stomach has formed, the clamps can be released.

International PCT publication number WO 2009/027860 teaches a suture retention hub that may be used as part of a suture clamp assembly as previously described. The retention hub includes a base with an aperture that extends therethrough. The hub also includes a handle pivotally mounted to a portion of the base. The handle also includes an aperture. When a suture is received through the base and handle apertures, and the handle is in a released configuration, the retention hub may be slid along a length of suture. When the handle is rotated toward the base, the suture may be frictionally crimped, and is prevented from further movement through the hub. The device appears to include a lock for preventing the handle from moving from the crimped position back to the released sliding configuration. The suture retention hub appears to include several drawbacks, including an apparent need for relatively tight geometrical tolerances in order to work as described, and may have difficulty in initially receiving a suture thread, even while in its open sliding configuration. The device also appears relatively complex and expensive to manufacture.

The present disclosure is directed toward one or more of the problems set forth above.

SUMMARY OF THE DISCLOSURE

In one aspect, a gastrointestinal suture anchor set device includes a pusher slidably received in a needle. A suture clamp assembly includes an anchor attached to one end of a length of suture, which is slidably received in a sequence of passages defined by a suture clamp in a high profile sliding configuration. The anchor is received in one end of the needle, with the suture extending outside of the needle. The clamp includes a series of disks movable to a low profile clamped configuration at which different segments of the suture are clamped between faces of adjacent disks. The series of disks define a sequence of suture passages that are segments of a tortuous pathway through the clamp traversed by the suture.

In another aspect, a suture clamp includes a series of disks movable from a high profile sliding configuration to a low profile clamped configuration. The series of disks define a sequence of suture passages that are segments of a tortuous pathway through the suture clamp. Each of the suture passages extends between opposite faces of one of the disks. The tortuous pathway includes different segments between faces of adjacent disks connecting consecutive suture passages when in the low profile clamped configuration.

In still another aspect, a method of treating a patient includes piercing through the abdominal skin into the stomach of the patient with a needle of a gastrointestinal suture anchor set device. An anchor of the device is deployed into the stomach by advancing a pusher through the needle. The needle is withdrawn from the patient leaving a segment of suture extending from the patient into the stomach with one end attached to the anchor. The stomach is pulled against the abdominal wall by tensioning the suture. A suture clamp in a high profile sliding configuration is slid along the suture toward the anchor such that the suture moves through a sequence of suture passages that are segments of a tortuous pathway through the clamp. The suture is clamped in the clamp by moving the suture clamp from the high profile sliding configuration to a low profile clamped configuration such that different segments of the suture are clamped between faces of adjacent disks of the clamp while a segment of the suture between the anchor and clamp remains in tension.

DETAILED DESCRIPTION

Figure 1:
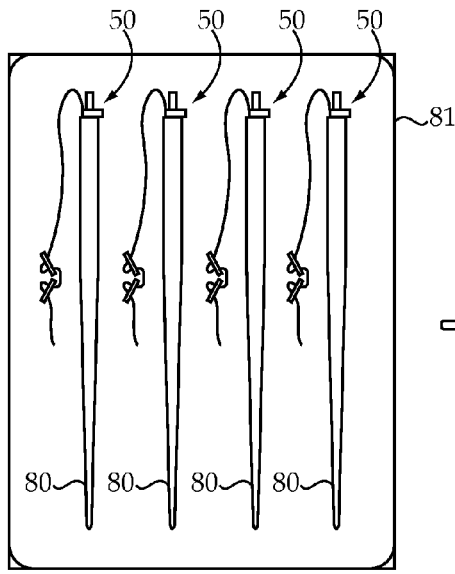
FIG. 1 is a top view of a sterilized package containing four gastrointestinal suture anchor set devices according to the present disclosure.
Figure 2:
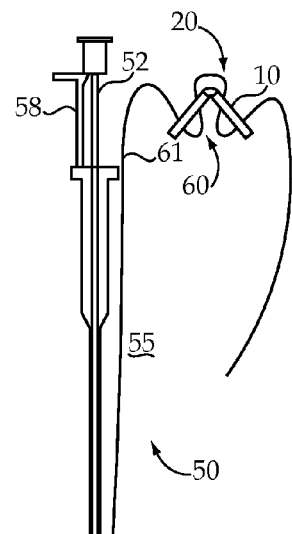
FIG. 2 is a side sectioned view of a gastrointestinal suture anchor set device from the package of FIG. 1 with its blunt end holder removed.

FIG. 1 shows an example commercial embodiment according to the present disclosure in which four gastrointestinal suture anchor set devices 50 share a common sterilized package 81. Each of the suture anchor set devices 50 may be protectively housed in a blunt end holder 80 to cover the relatively sharp needle tip housed therein. The sterilized package 81 may contain four suture anchor set devices 50 in order to provide the health care practitioner with the three used in a typical application and an extra in case a problem occurs such that four are needed instead of three. In any event, those skilled in the art will appreciate that the gastrointestinal suture anchor set devices 50 according to the present disclosure could be individually packaged, or packaged in different multiples without departing from the scope of the present disclosure. FIG. 2 shows a sectioned view of one of the gastrointestinal suture anchor set devices 50 with the blunt end holder 80 slidably removed to reveal a pusher 52 that is slidably received in a needle 51. A suture clamp assembly 60 includes an anchor 62 attached to one end 64 of a length of suture 61. The anchor 62 is received in one end 54 of needle 51, with the suture 61 extending outside 55 of the needle 51. The length of suture 61 is slidably received in a sequence of passages defined by a suture clamp 10 in a high profile sliding configuration 20. When in the high profile sliding configuration 20, suture clamp 10 may be easily grasped and slid along the length of suture 61.

Figure 6:
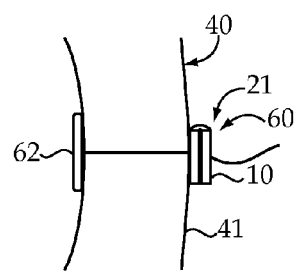
FIG. 6 is a sectioned side view of the patient similar to FIG. 5 after the suture clamp has been slid along the suture and moved from its sliding configuration to its low profile clamped configuration adjacent the patient's skin.
Figure 7:
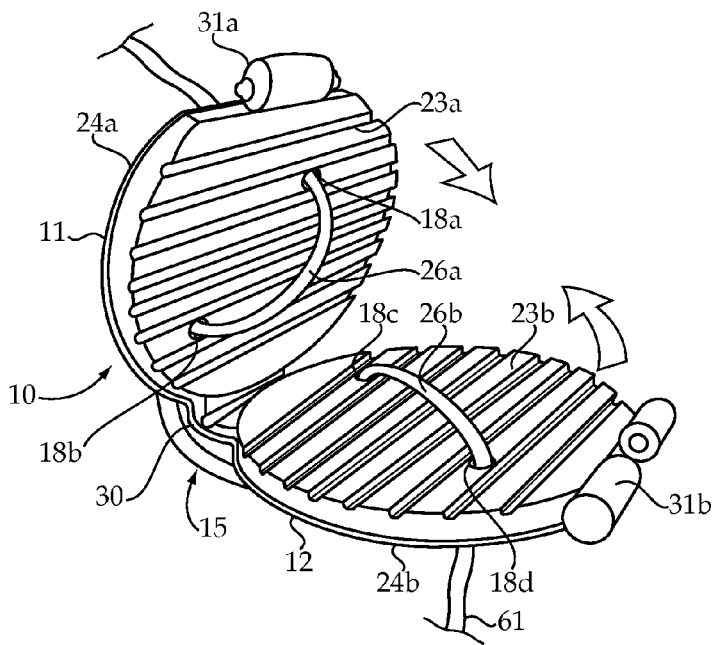
FIG. 7 is a perspective view of a suture clamp in a high profile sliding configuration according to one embodiment of the present disclosure.

Referring to FIG. 7, the suture clamp 10 according to one example embodiment is shown enlarged in the high profile sliding configuration 20. In particular, suture clamp 10 includes a series of disks 11 and 12 defining a sequence of suture passages 18a-c that are segments of a tortuous pathway 15 through suture clamp 10 that is traversed by suture 61. The suture passages 18a-c may be distributed in any suitable pattern. However, if the suture passages 18a-c are offset relative to each other, this might prevent suture overlapping when the suture clamp is moved to its low profile clamped configuration. In some instances, avoiding suture overlap may assist in avoiding suture slip. Suture clamp 10 is traversed by suture 61. Suture clamp 10 is movable to a low profile clamped configuration 21 (FIG. 6) at which different segments 26a and 26b of suture 61 are clamped, without overlapping each other, between faces 23a and 23b of disks 11 and 12, respectively. Faces 23a and 23b may include some suitable texturing that assists in better gripping of suture 61 when the faces 23a and 23b are brought together to clamp onto the non-overlapping segments 26a and 26b of suture 61. Nevertheless, non-overlapping suture segments would also fall within the intended scope of the disclosure. In the illustrated embodiment, faces 23a and 23b are formed to include a series of horizontal ridges and valleys that are oriented at an angle with regard to suture segments 26a and 26b in order to increase friction on, and prevent slippage of, suture 61.

In the case of suture clamp 10, the pair of disks 11 and 12 are joined by a hinge 30, which may be living hinge if suture clamp 10 is molded from a homogenous integral piece of plastic. For instance, suture clamp 10 may be injection molded as a single piece from polypropylene or polyethylene due to their suitability for snap fit and living hinge applications. Other plastics would also fall within the intended scope of this disclosure as well. The structure of the hinge 133 and clamp 134 might be such that protuberances on hinge path 133b are received in counterpart indents on the hinge half 133a in a manner similar to the described clasp associated with the embodiment of FIG. 7. In addition, disks 11 and 12 may also be joined with a clasp 31 when suture clamp 10 is in the low profile clamped configuration 21 as shown in FIG. 6. Clasp 31 may consist of a first half 31a integral with disk 11 and a second half 31b integral with disk 12. Portion 31a may include protuberances on either side that are received as snap fit detents into concave portions on the inner facing ends of the other clamp half 31b. In this way, the clasp snaps into place and resists reopening once the suture clamp 10 is placed in the low profile clamped configuration 21 as shown in FIG. 6. Suture clamp 10 is also notable for showing that each of the disks 11 and 12 defines two offset suture passages 18a-b and 18c-d, respectively, that each extend between opposite faces 23a, b and 24a, b, respectively. Preferably the diameter of suture passages 18 are larger than the diameter of suture 61 so that the suture can slide easily therethrough when the suture clamp 10 is in the high profile sliding configuration 20 as shown in FIGS. 2 and 7. It is also important to note that in the suture clamp 10 of FIG. 7, suture passages 18a and 18b are non-consecutive segments of tortuous pathway 15. In other words, the segment of suture 61 extending through passage 18a is separated from the segment of suture 61 passing through passage 18b by suture segment 26a. Likewise, the segment of suture 61 through passage 18c is separated from the segment through passage 18d by suture segment 26b. Thus, the tortuous pathway 15 through the suture clamp 10 of FIG. 7 includes two internal segments 26a and 26b and also and external segment that extends between passage 18b and 18c. Suture clamp 10 may include relatively sharp corner surfaces on faces 23a and 23b to assist in gripping suture 61, but may include relatively soft curved corners and edges on all exposed surfaces when suture clamp 10 is in the low profile clamped configuration 21 so as not to irritate a patient or provide sharp corners that could catch on something, such as clothing that may make contact with suture clamp 10. When in the low profile clamped configuration 21, suture clamp 10 may have dimensions resembling a button with a diameter of about a half inch in thickness on the order of about a tenth of an inch. Nevertheless, the dimensions of the suture clamp 10 may scale or be changed to suit any particular surgical procedure without departing from the present disclosure. In addition, suture clamp 10 may be partially or entirely overmolded with silicone if deemed desirable for better patient comfort. Although the clamping faces 23a and 23b are shown are being relatively planar with texturing, curved and/or untextured faces would also fall within the intended scope of the present disclosure.

Figure 9:
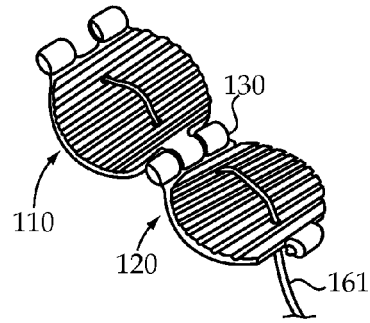
FIG. 9 is a perspective view of the suture clamp of FIG. 8 in its high profile sliding configuration.
Figure 8:
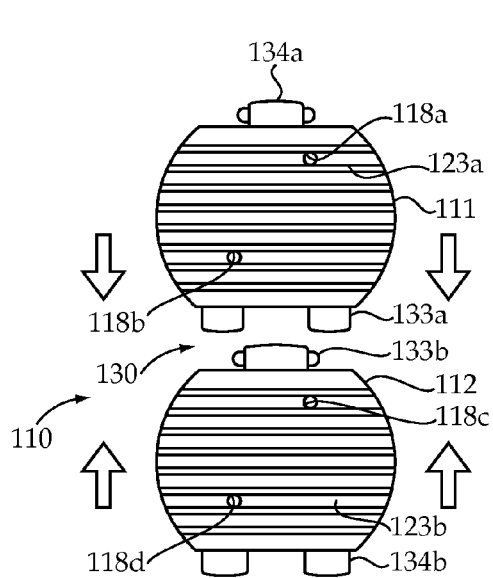
FIG. 8 is a perspective view of a suture clamp according to a second embodiment of the present disclosure, prior to assembly.
Figure 10:
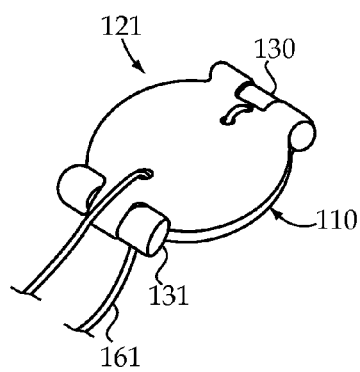
FIG. 10 is a perspective view of the suture clamp of FIGS. 8 and 9 after being moved to its low profile clamped configuration.

Referring to FIGS. 8-10, a suture clamp 110 according to a second embodiment of the present disclosure includes identical first and second disks 111 and 112 that each include half of a hinge 133 and half of a clasp 134. In particular, disk 111 includes half of a hinge 133a that integrally extends from one edge of disk 111 and a second half of the hinge 133b that extends from the edge of disk 112. Suture clamp 110 may include an offset hole pattern 118a-d similar to the suture clamp 10 described with regard to FIG. 7. However, suture clamp 110 differs from the earlier embodiment in that each disk is identical and each includes half of the hinge 133 and half of the clasp 134. Thus, both the hinge 133 and clamp 134 have identical structures, but only the hinge portion is mated when the suture clamp 110 is in its high profile sliding configuration 120 as shown in FIG. 9. The design of suture clamp 110 allows for a single mold for one of the disks 111 or 112 to be made from a suitable molded plastic. Any two of the formed disks may then be joined to form a suture clamp 110 according to this embodiment of the present disclosure. Thus, geometry of hinge 133 and clasp 134 may be substantially identical to the structure of clasp 31 for suture clamp 10 described earlier.

Figure 11:
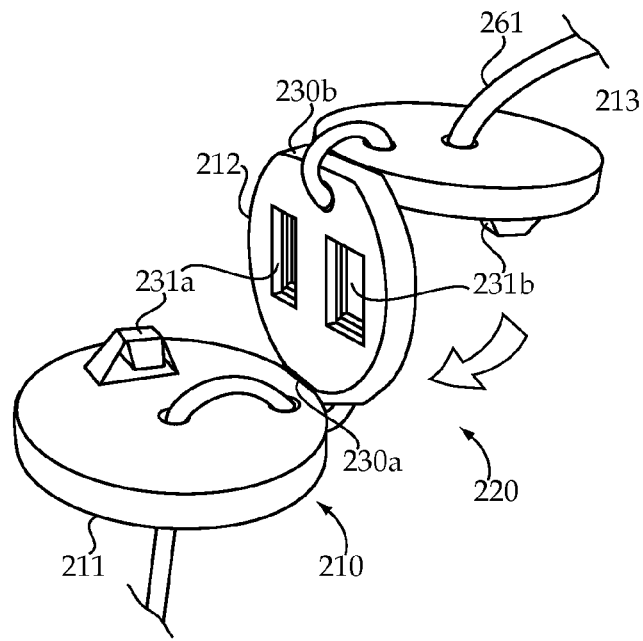
FIG. 11 is a perspective view of a suture clamp according to still another embodiment of the present disclosure in its high profile sliding configuration.
Figure 12:
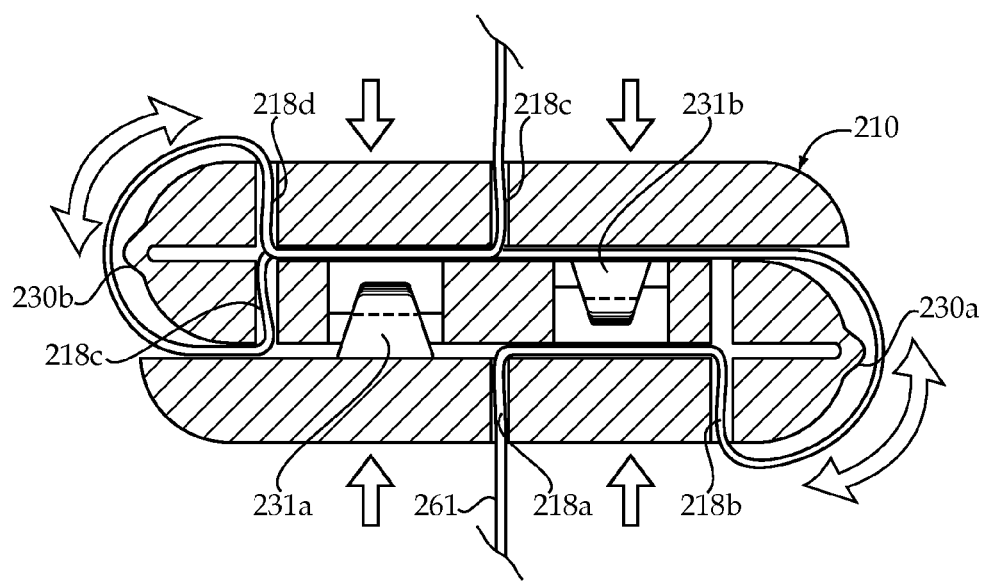
FIG. 12 is a sectioned view through the suture clamp of FIG. 11 after being moved to its low profile clamped configuration.

Referring to FIGS. 11 and 12, a suture clamp 210 according to still another embodiment of the present disclosure includes a series of three disks 211, 212 and 213 that are interconnected by living hinges 230a and 230b. In this example, each pair of disks 211 and 212, 212 and 213 include a clasp 231a and 231b, respectively, that take the form of a hook that engages an edge formed in middle disk 212. The hook portions of clasp 231a and 231b are formed on the end disks 211 and 213, respectively. As with the previous embodiments, the series of disks 211/212 and 212/213 define a sequence of passages 218a-e that define non-consecutive segments of a tortuous pathway 215 through suture clamp 210. Suture clamp 210 is shown in its high profile sliding configuration in FIG. 11 and in a sectioned view in FIG. 12 in its low profile clamped configuration 221. Also, as in the previous embodiments, segments of suture 261 are clamped or pinched between adjacent faces of adjacent disks to inhibit sliding on suture 261 when in the low profile clamped configuration 221 is shown in FIG. 12. In all disclosed embodiments, the combination of the tortuous path through the suture clamp and the friction created by the clamping faces onto the suture combine to lock the suture in place and prevent the sliding of the same after being place in the low profile clamped configuration.

INDUSTRIAL APPLICABILITY

Suture clamps according to the present disclosure may find potential application in any surgical situation where a suture clamp may be needed. The present disclosure finds particular application in relation to suture clamps for use in gastrointestinal suture anchor set devices. In such a situation, the suture clamp may bear against the skin of the patient while a tract forms between the outside of the patient's body and their stomach for easier access to the stomach via a gastric catheter or feeding tube.

Figure 3:
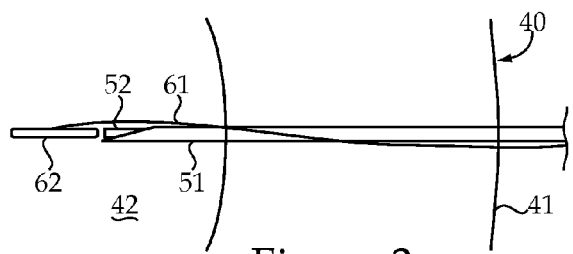
FIG. 3 is a side sectioned view through a patient with the anchor being deployed from the distal end of the needle of the gastrointestinal suture anchor set device of FIG. 2.
Figure 4:
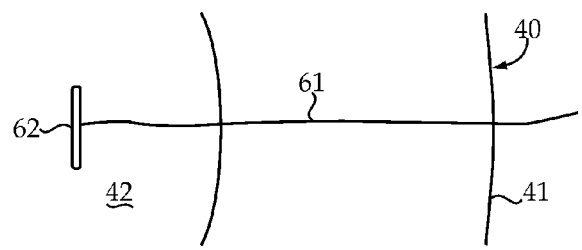
FIG. 4 is a side sectioned view through the patient similar to FIG. 3 after the needle has been withdrawn from the patient leaving the anchor in the patient's stomach with the attached suture extending out of the patient.
Figure 5:
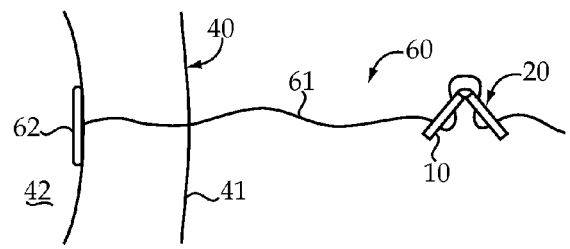
FIG. 5 is a view similar to FIG. 4 after tensioning the suture to lift the patient's stomach toward their abdominal wall.

Referring to FIGS. 1-6, a method of using a gastrointestinal suture anchor set device 50 according to the present disclosure may begin by opening sterilized package 81 and removing one of the devices so therefrom. Thereafter, the blunt end holder 80 may be removed to reveal the sharp end of needle 51. The health care provider may then initiate treatment of the patient 40 by piercing through the abdominal skin 41 into the stomach 42 of the patient with needle 51 of the gastrointestinal suture anchor set device 50. after confirming proper placement, the anchor 62 is then deployed in the patient's stomach 42 by advancing pusher 52 through needle 51 as shown in FIG. 3. Next, the needle 51 is withdrawn from the patient 40 leaving a segment of suture 61 extending from outside the patient into the stomach 42, with one end attached to the anchor 62. Next, the stomach 42 of the patient is pulled against the abdominal wall by tensioning the suture 61 so that anchor 62 bears against the wall of the patient's stomach 42 as best shown in FIG. 5. Next, the suture clamp 10 is slid while in a high profile sliding configuration 20 along suture 61 toward anchor 62. When this occurs, the suture 61 moves through a sequence of suture passages 18 that are segments of a tortuous pathway 15 through the suture clamp 10. Finally, when the suture clamp 10 is in proper position adjacent the skin 41 of the patient 40, the suture clamp 10 is moved from its high profile sliding configuration 20 to its low profile clamped configuration 21 as best shown in FIG. 6. When this is done, different segments of the suture 26a and 26b are clamped between faces 23a and 23b of adjacent disks 11 and 12 of suture clamp 10 while a segment of the suture between anchor 62 and suture clamp 10 remains in tension. Thereafter, the excess portion of suture 61 extending away from suture clamp 10 can be trimmed away. This procedure may be twice more repeated until forming a triangular pattern on the patient's abdomen for surrounding a central location for placement of a gastric catheter or feeding tube in a known manner. As described, when the suture clamp is moved from its high profile sliding configuration 20 to its low profile clamped configuration 21, adjacent disks 11, 12 are pivoted toward each other about a hinge 30 that connects the adjacent disks. The suture clamp 10 is maintained in its low profile clamped configuration by also joining adjacent disks 11 and 12 with a clasp 31 positioned opposite to hinge 30. The embodiments of the suture clamp 110 and 210 shown in FIGS. 8-12 have slightly different forms but function in a manner similar to that described with regard to the suture clamp 10 shown in FIGS. 1-7.

It should be understood that the above description is intended for illustrative purposes only, and is not intended to limit the scope of the present disclosure in any way. For instance, suture passages through the disks that are aligned as opposed to being offset, as shown, would also fall within the intended scope of the present disclosure. Thus, those skilled in the art will appreciate that other aspects of the disclosure can be obtained from a study of the drawings, the disclosure and the appended claims.

What is claimed is:

1. A gastrointestinal suture anchor set device comprising:
   a needle;
   a pusher slidably received in the needle;
   a suture clamp assembly with an anchor attached to one end of a length of suture, which is slidably received in a sequence of suture passages defined by a clamp in a high profile sliding configuration;
   the anchor being received in one end of the needle with the suture extending outside of the needle;
   the clamp includes a series of disks movable to a low profile clamped configuration at which different segments of the suture are clamped between faces of adjacent disks;
   each disk of the series of disks having opposite faces separated by a thickness of the disk, and each of the suture passages extending through the thickness between the opposite faces of one of the disks; and
   the series of disks defining the sequence of suture passages that are segments of a tortuous pathway through the clamp traversed by the suture, and the tortuous pathway includes different segments between faces of adjacent disks connecting consecutive suture passages when in the low profile clamped configuration.

2. The device of claim 1 wherein the series of disks is a single pair of disks joined by a hinge.

3. The device of claim 2 wherein the disks are also joined by a clasp in the low profile clamped configuration.

4. The device of claim 3 wherein the hinge is a living hinge and the clamp is a homogenous integral piece of plastic.

5. The device of claim 3 wherein the pair of disks are identical to each other, with each including half of the hinge and half of the clasp.

6. The device of claim 3 wherein the needle, the pusher, the anchor and a segment of the suture are received in a blunt end holder which is received in a sterilized package.

7. The device of claim 3 wherein each of the pair of disks defines two suture passages that each extend between opposite faces of the disk.

8. The device of claim 7 wherein the two suture passages offset relative to each other and are nonconsecutive segments of the tortuous pathway.

9. A suture clamp comprising:
- a series of disks movable from a high profile suture sliding configuration to a low profile clamped configuration;
- the series of disks defining a sequence of suture passages that are segments of a tortuous pathway through the suture clamp;
- each disk of the series of disks having opposite faces separated by a thickness of the disk;
- each of the suture passages extending through the thickness between the opposite faces of one of the disks;
- the tortuous pathway includes different segments between faces of adjacent disks connecting consecutive suture passages when in the low profile clamped configuration.

10. The suture clamp of claim 9 wherein the series of disks is a single pair of disks joined by a hinge.

11. The suture clamp of claim 10 wherein the disks are also joined by a clasp in the low profile suture clamped configuration.

12. The suture clamp of claim 11 wherein the hinge is a living hinge and the suture clamp is a homogenous integral piece of plastic.

13. The suture clamp of claim 11 wherein the pair of disks are identical to each other, with each including half of the hinge and half of the clasp.

14. The suture clamp of claim 11 wherein each of the pair of disks defines two of the suture passages that each extend between opposite faces of the disk.

15. The suture clamp of claim 14 wherein the two suture passages are offset relative to each other and are nonconsecutive segments of the tortuous pathway.

16. A method of treating a patient utilizing a suture clamp that includes a series of disks movable from a high profile suture sliding configuration to a low profile clamped configuration; the series of disks defining a sequence of suture passages that are segments of a tortuous pathway through the suture clamp; each disk of the series of disks having opposite faces separated by a thickness of the disk; each of the suture passages through the thickness between the opposite faces of one of the disks; the tortuous pathway includes different segments between faces of adjacent disks connecting consecutive suture passages when in the low profile clamped configuration, the method comprising the steps of:
- piercing through the abdominal skin into the stomach of the patient with a needle of a gastrointestinal suture anchor set device;
- deploying an anchor of the device into the stomach by advancing a pusher through the needle;
- withdrawing the needle from the patient leaving a segment of suture extending from outside the patient into the stomach with one end attached to the anchor;
- pulling the stomach against the abdominal wall of the patient by tensioning the suture;
- sliding the suture clamp in the high profile sliding configuration along the suture toward the anchor such that the suture moves through the sequence of suture passages that are segments of the tortuous pathway through the suture clamp; and
- clamping the suture in the suture clamp by moving the suture clamp from the high profile sliding configuration to a low profile clamped configuration such that different segments of the suture are clamped between faces of adjacent disks of the clamp while a segment of the suture between the anchor and the suture clamp remains in tension.

17. The method of claim 16 wherein the clamping step includes pivoting the adjacent disks toward each other about a hinge connecting the adjacent disks.

18. The method of claim 17 wherein the clamping step includes joining the adjacent disks with a clasp positioned opposite the hinge.

19. The method of claim 18 wherein each of the adjacent disks defines two suture passages that each extend between opposite faces of the disk.

20. The method of claim 19 wherein the two suture passages are offset to each other and are nonconsecutive segments of the tortuous pathway.

* * * * *